United States Patent
Kikuchi et al.

(10) Patent No.: US 9,920,083 B2
(45) Date of Patent: Mar. 20, 2018

(54) IMAGE RECORDING PAPER MEDIUM AND IMAGE RECORDING METHOD

(71) Applicant: FUJIFILM Corporation, Tokyo (JP)

(72) Inventors: Wataru Kikuchi, Kanagawa (JP); Yuji Yoshida, Kanagawa (JP); Ryuji Shinohara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/019,578

(22) Filed: Feb. 9, 2016

(65) Prior Publication Data

US 2016/0250866 A1    Sep. 1, 2016

(30) Foreign Application Priority Data

Feb. 27, 2015   (JP) ................ 2015-039095

(51) Int. Cl.
| | | |
|---|---|---|
| *C07F 9/38* | (2006.01) | |
| *C09D 5/00* | (2006.01) | |
| *B41M 5/52* | (2006.01) | |
| *B41M 7/00* | (2006.01) | |
| *C07F 9/11* | (2006.01) | |
| *C07F 9/113* | (2006.01) | |
| *C07F 9/12* | (2006.01) | |

(52) U.S. Cl.
CPC ......... *C07F 9/3808* (2013.01); *B41M 5/5227* (2013.01); *B41M 7/009* (2013.01); *C07F 9/11* (2013.01); *C07F 9/113* (2013.01); *C07F 9/12* (2013.01); *C07F 9/3834* (2013.01); *C07F 9/3843* (2013.01); *C09D 5/002* (2013.01)

(58) Field of Classification Search
CPC ..... B41M 5/52; B41M 5/5218; B41M 5/5227
See application file for complete search history.

(56) References Cited

U.S. PATENT DOCUMENTS

| 8,919,943 B2 | 12/2014 | Ikegami et al. |
| 2011/0187789 A1 | 8/2011 | Saito |
| 2012/0194621 A1 | 8/2012 | Ikegami et al. |

FOREIGN PATENT DOCUMENTS

| JP | H05-50741 A | 3/1993 | |
| JP | 2001-071634 A | 3/2001 | |
| JP | 2001-277704 A | 10/2001 | |
| JP | 2005-220506 A | 8/2005 | |
| JP | 2006123316 A * | 5/2006 | ............ B41M 5/00 |
| JP | 2011-161643 A | 8/2011 | |
| JP | 2012-176602 A | 9/2012 | |
| JP | 2013-180534 A | 9/2013 | |

OTHER PUBLICATIONS

Sawada et al., Anti-Fading Agent of Image and Medium to be Recorded by Jetting Ink, May 18, 2016.*
An Office Action; "Decision of Refusal," issued by the Japanese Patent Office dated Jan. 9, 2018, which corresponds to Japanese Patent Application No. 2015-039095 and is related to U.S. Appl. No. 15/019,578; with English translation.
An Office Action issued by the Japanese Patent Office dated Oct. 3, 2017, which corresponds to Japanese Patent Application No. 2015-039095 and is related to U.S. Appl. No. 15/019,578; with English translation.

* cited by examiner

*Primary Examiner* — Betelhem Shewareged
(74) *Attorney, Agent, or Firm* — Studebaker & Brackett PC

(57) ABSTRACT

The image recording paper medium contains at least one kind of organic phosphorus compound selected from an organic phosphonic acid represented by the following Formula (1), a salt thereof, an organic phosphoric acid represented by the following Formula (2), and a salt thereof.

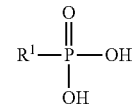

Formula (1)

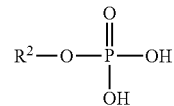

Formula (2)

In the formulae, each of $R^1$ and $R^2$ independently represents an unsubstituted alkyl group, an unsubstituted cycloalkyl group, an unsubstituted alkenyl group, or an aryl group.

13 Claims, No Drawings

IMAGE RECORDING PAPER MEDIUM AND IMAGE RECORDING METHOD

CROSS-REFERENCE TO RELATED APPLICATION

The present application claims priority under 35 U.S.C. § 119 to Japanese Patent Application No. 2015-039095, filed on Feb. 27, 2015. The above application is hereby expressly incorporated by reference, in its entirety, into the present application.

BACKGROUND OF THE INVENTION

1. Field of the Invention

The present invention relates to an image recording paper medium and an image recording method.

2. Description of the Related Art

As image recording methods for forming an image on a recording medium such as paper based on an image data signal, there are recording methods such as an electrophotographic method, sublimation-type and melting-type thermal transfer methods, and an ink jet method.

In the ink jet recording method, a printing plate is not required, and an image is directly formed on a recording medium by ejecting an ink only to an image forming portion. Therefore, in this method, the ink can be efficiently used, and the running cost is low. Furthermore, a printing device used in the ink jet recording method is relatively cheaper than a printer used in the related art, can be downsized, and reduces noise. In this way, the ink jet recording method has various advantageous compared to other image recording methods.

When an image is recorded on a recording medium by the ink jet recording method, the moisture in an aqueous ink permeates the recording medium. It is known that the moisture permeating the recording medium cleaves hydrogen bonds of cellulose constituting a pulp layer of the recording medium, the cleaved hydrogen bonds are recombined after the moisture dries, and this leads to a phenomenon (curling or cockling) in which the recording medium is deformed.

To prevent the deformation of the recording medium, a method of adding an anti-curl agent such as a saccharide to an ink, a method of forcibly preventing the curling or cockling by using a paper pressing mechanism of a transport portion, and the like have been suggested. However, none of these methods has succeeded in sufficiently preventing the deformation of the recording medium.

Meanwhile, JP2013-180534A discloses that by coating beforehand a recording medium with a liquid composition containing a specific isocyanate compound, it is possible to prevent the deformation of the recording medium at the time of recording an image on the recording medium by using an aqueous ink.

SUMMARY OF THE INVENTION

However, the isocyanate compound described in JP2013-180534A is highly reactive and causes a safety problem when the isocyanate compound is present in the recording medium.

An object of the present invention is to provide an image recording paper medium which is effectively prevented from being deformed after an image is formed thereon by using an aqueous ink, enables a high-resolution image to be formed thereon, and is excellent in a degree of glossiness of the image formed thereon and in safety.

Another object of the present invention is to provide an image recording method which makes it possible to effectively prevent a paper medium from being deformed after an image is formed thereon by using an aqueous ink and to form a high-resolution image having an excellent degree of glossiness.

To achieve the aforementioned objects, the inventors of the present invention repeated intensive investigation. As a result, they obtained knowledge that a recording medium, which is obtained by coating a paper medium with a solution containing a specific organic phosphorus compound, is effectively prevented from curling after an image is formed thereon by using an aqueous ink, a high-resolution image can be formed on such a recording medium, and a degree of glossiness of the formed image is excellent.

Based on this knowledge, the inventors further repeated investigation and accomplished the present invention.

The aforementioned objects of the present invention were achieved by the following means.

[1] An image recording paper medium containing at least one of organic phosphorus compound selected from an organic phosphonic acid represented by the following Formula (1), a salt of the organic phosphonic acid, an organic phosphoric acid represented by the following Formula (2), and a salt of the organic phosphoric acid.

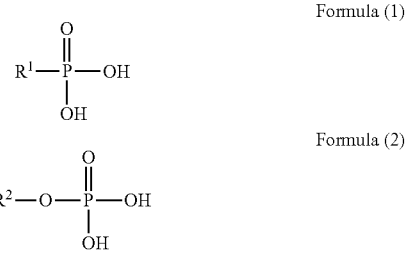

In the formulae, each of $R^1$ and $R^2$ independently represents an unsubstituted alkyl group, an unsubstituted cycloalkyl group, an unsubstituted alkenyl group, or an aryl group.

[2] The image recording paper medium described in [1], in which each of $R^1$ and $R^2$ represents an unsubstituted alkyl group having 6 to 24 carbon atoms.

[3] The image recording paper medium described in [1] or [2] including a coat layer containing calcium carbonate, in which the coat layer contains the organic phosphorus compound.

[4] The image recording paper medium described in [3], in which the content of the organic phosphorus compound contained in the coat layer is 1 part by mass to 30 parts by mass with respect to 100 parts by mass of the content of the calcium carbonate contained in the coat layer.

[5] The image recording paper medium described in any one of [1] to [4] that is obtained by coating the coat layer of the paper medium having the coat layer containing calcium carbonate with a solution containing the organic phosphorus compound.

[6] An image recording method including a step (a) of coating a paper medium with a solution containing at least one of organic phosphorus compound selected from an organic phosphonic acid represented by the following Formula (1), a salt of the organic phosphonic acid, an organic phosphoric acid represented by the following Formula (2), and a salt of the organic phosphoric acid, and a step (b) of forming an image by ejecting an aqueous ink by an ink jet method onto the surface of the paper medium that is coated with the solution.

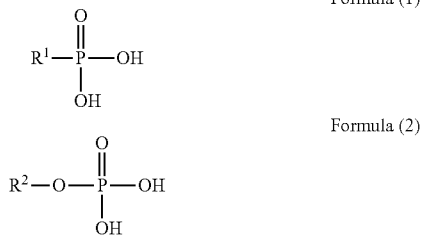

Formula (1)

Formula (2)

In the formulae, each of $R^1$ and $R^2$ independently represents an unsubstituted alkyl group, an unsubstituted cycloalkyl group, an unsubstituted alkenyl group, or an aryl group.

[7] The image recording method described in [6], in which each of $R^1$ and $R^2$ represents an unsubstituted alkyl group having 6 to 24 carbon atoms.

[8] The image recording method described in [6] or [7], in which in the step (a), the amount of the organic phosphorus compound coating the paper medium is equal to or less than 10 g/m².

[9] The image recording method described in any one of [6] to [8], in which the paper medium has a coat layer containing calcium carbonate, and the step (a) is a step of coating the coat layer with a solution containing the organic phosphorus compound.

[10] The image recording method described in [9], in which the amount of the organic phosphorus compound coating the coat layer is 1 part by mass to 30 parts by mass with respect to 100 parts by mass of the content of the calcium carbonate contained in the coat layer.

[11] The image recording method described in any one of [6] to [10] further including a step of fixing the formed image by heating after the step (b).

In the present specification, a range of numerical values described by using "to" means a range which includes numerical values listed before and after "to" as a lower limit value and an upper limit value.

The image recording paper medium of the present invention is a paper medium which is effectively prevented from being deformed by the permeation of moisture after an image is formed thereon by using an aqueous ink, enables a high-resolution image to be formed thereon, and is excellent in a degree of glossiness of the formed image and in safety. Furthermore, according to the image recording method of the present invention, it is possible to effectively prevent a paper medium from being deformed by the permeation of moisture at the time of forming an image by ejecting an aqueous ink to the paper medium and to form a high-resolution image having an excellent degree of glossiness.

DESCRIPTION OF THE PREFERRED EMBODIMENTS

[Image Recording Paper Medium]

The image recording paper medium of the present invention contains at least one kind of organic phosphorus compound (hereinafter, also referred to as a "specific organic phosphorus compound) selected from an organic phosphonic acid represented by the following Formula (1), a salt of the organic phosphonic acid represented by the following Formula (1), an organic phosphoric acid represented by the following Formula (2), and a salt of the organic phosphoric acid represented by the following Formula (2).

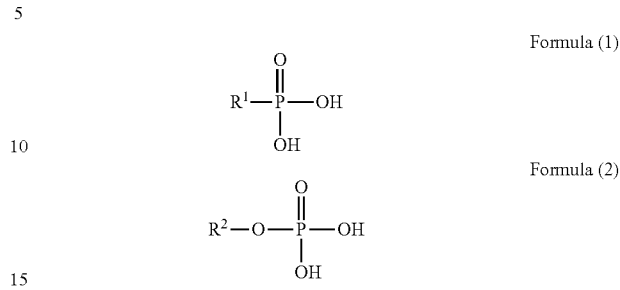

Formula (1)

Formula (2)

In Formulae (1) and (2), each of $R^1$ and $R^2$ independently represents an unsubstituted alkyl group, an unsubstituted cycloalkyl group, an unsubstituted alkenyl group, or an aryl group.

The unsubstituted alkyl group which can be adopted as $R^1$ and $R^2$ is not particularly limited and may be linear or branched. That is, in the present invention, the "unsubstituted alkyl group" also means an alkyl group having an alkyl group as a substituent (that is, a branched alkyl group).

The unsubstituted alkyl group which can be adopted as $R^1$ and $R^2$ preferably has 6 to 24 carbon atoms, more preferably has 6 to 20 carbon atoms, even more preferably has 6 to 18 carbon atoms, still more preferably has 8 to 15 carbon atoms, and yet more preferably has 8 to 12 carbon atoms. Specific examples of the unsubstituted alkyl group include propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and icosyl groups, heneicosyl, docosyl, tricosyl, tetracosyl, methylpentyl, methylhexyl, methylheptyl, methyloctyl, methylnonyl, methylundecyl, methylheptadecyl, ethylhexadecyl, methyloctadecyl, propylpentadecyl, hexyldecyl, octyldodecyl, and heptylundecyl. Among these, octyl, decyl, dodecyl, octadecyl, or 2-ethylhexyl is preferable.

The unsubstituted cycloalkyl group which can be adopted as $R^1$ and $R^2$ preferably has 3 to 8 carbon atoms, more preferably has 5 to 8 carbon atoms, and even more preferably has 6 to 8 carbon atoms. Preferred examples of the unsubstituted alkyl group specifically include cyclopentyl, cyclohexyl, cycloheptyl, and cyclooctyl.

The unsubstituted alkenyl group which can be adopted as $R^1$ and $R^2$ is not particularly limited and may be linear or branched. That is, in the present invention, the "unsubstituted alkenyl group" also means an alkenyl group having an alkyl group as a substituent (that is, a branched alkenyl group). The unsubstituted alkenyl group which is included in the unsubstituted alkenyl group of the present invention and can be adopted as $R^1$ and $R^2$ preferably has 6 to 24 carbon atoms, more preferably has 6 to 20 carbon atoms, even more preferably has 6 to 18 carbon atoms, still more preferably has 8 to 18 carbon atoms, and yet more preferably has 10 to 18 carbon atoms. Preferred examples of the unsubstituted alkenyl group specifically include hexenyl, heptenyl, octenyl, decenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, isotridecenyl, isooctadecenyl, isotriacontenyl, butyloctenyl, hexyldecenyl, octyldodecenyl, decyltetradecenyl, and dodecylhexadecenyl. Among these, decenyl or octyldodecenyl is preferable.

When each of $R^1$ and $R^2$ represents an alkyl group, a cycloalkyl group, or an alkenyl group, if these groups has a substituent, the hydrophobicity of the organic phosphorus compound is enhanced, and thus the organic phosphorus compound is easily localized on the surface layer of the paper medium, or the degree of glossiness deteriorates in some cases. Alternatively, inversely, the hydrophilicity of the organic phosphorus compound is enhanced, and thus a moisture blocking effect is not sufficiently obtained in some cases. In the present invention, when each of $R^1$ and $R^2$ represents an alkyl group, a cycloalkyl group, or an alkenyl group, all of these groups are unsubstituted.

The aryl group which can be adopted as $R^1$ and $R^2$ is not particularly limited, and the aryl group preferably has 6 to 20 carbon atoms, more preferably has 6 to 15 carbon atoms, and even more preferably has 6 to 12 carbon atoms. The aryl group is preferably a naphthyl group or a phenyl group, and more preferably a phenyl group. The aryl group which can be adopted as $R^1$ and $R^2$ may have a substituent, and as the substituent, a group selected from the group consisting of an alkyl group (an alkyl group preferably having 1 to 10 carbon atoms, more preferably having 1 to 6 carbon atoms, and even more preferably having 1 to 4 carbon atoms), a hydroxy group, an amino group, an alkyl group, and a halogen atom is preferable. The aryl group which can be adopted as $R^1$ and $R^2$ is preferably unsubstituted.

Particularly, each of $R^1$ and $R^2$ preferably represents an unsubstituted alkyl group having 6 to 24 carbon atoms, and more preferably an unsubstituted alkyl group having 8 to 18 carbon atoms.

Specific examples of the organic phosphonic acid represented by Formula (1) include ethyl phosphonate, n-propyl phosphonate, i-propyl phosphonate, n-butyl phosphonate, t-butyl phosphonate, hexyl phosphonate, octyl phosphonate, decyl phosphonate, n-octadecyl phosphonate, phenyl phosphonate, o-methyl-phenyl phosphonate, m-methyl-phenyl phosphonate, p-methyl-phenyl phosphonate, o-ethyl-phenyl phosphonate, m-ethyl-phenyl phosphonate, p-ethyl-phenyl phosphonate, o-t-butyl-phenyl phosphonate, m-t-butyl-phenyl phosphonate, p-t-butyl-phenyl phosphonate, p-hydroxy-phenyl phosphonate, m-hydroxy-phenyl phosphonate, o-hydroxy-phenyl phosphonate, 2,2-dimethylpropyl phosphonate, cyclohexyl phosphonate, n-hexyl phosphonate, o-aminophenyl phosphonate, m-aminophenyl phosphonate, p-aminophenyl phosphonate, o-chlorophenyl phosphonate, m-chlorophenyl phosphonate, p-chlorophenyl phosphonate, o-bromophenyl phosphonate, m-bromophenyl phosphonate, p-bromophenyl phosphonate, and oleyl phosphonate (octadecenyl phosphonate). From the viewpoint of further improving the effects of the present invention, an organic phosphonic acid selected from hexyl phosphonate, octyl phosphonate, decyl phosphonate, and n-octadecyl phosphonate is preferable.

Specific examples of the organic phosphoric acid represented by Formula (2) include ethyl phosphate, n-propyl phosphate, i-propyl phosphate, n-butyl phosphate, t-butyl phosphate, hexyl phosphate, octyl phosphate, decyl phosphate, dodecyl phosphate, n-octadecyl phosphate, 2-ethylhexyl phosphate, oleyl phosphate (octadecenyl phosphate), phenyl phosphate, o-methyl-phenyl phosphate, m-methyl-phenyl phosphate, p-methyl-phenyl phosphate, o-ethyl-phenyl phosphate, m-ethyl-phenyl phosphate, p-ethyl-phenyl phosphate, o-t-butyl-phenyl phosphate, m-t-butyl-phenyl phosphate, p-t-butyl-phenyl phosphate, p-hydroxy-phenyl phosphate, m-hydroxy-phenyl phosphate, o-hydroxy-phenyl phosphate, 2,2-dimethylpropyl phosphate, cyclohexyl phosphate, o-aminophenyl phosphate, m-aminophenyl phosphate, p-aminophenyl phosphate, o-chlorophenyl phosphate, m-chlorophenyl phosphate, p-chlorophenyl phosphate, o-bromo-phenyl phosphate, m-bromophenyl phosphate, and p-bromophenyl phosphate. From the viewpoint of further improving the effects of the present invention, an organic phosphoric acid selected from 2-ethylhexyl phosphate, dodecyl phosphate, and octadecyl phosphate is preferable.

The salt of the organic phosphonic acid represented by Formula (1) is not particularly limited, and preferred examples thereof include an alkali metal salt (such as a lithium salt, a sodium salt, or a potassium salt), an alkaline-earth metal salt (preferably a calcium salt or a magnesium salt), and an amine salt of the organic phosphonic acid represented by Formula (1).

The amine salt may be an ammonium salt or an organic amine salt. Examples of the organic amine salt include a trialcoholamine salt (such as a triethanolamine salt or a triisopropanolamine salt) and a dialkylalcohol amine salt (such as a methanol amine salt, dimethylaminoethanol salt, or a dibutylethanolamine salt). Among the above salts, an alkali metal salt is preferably, a sodium salt or a potassium salt is more preferable, and a sodium salt is even more preferable.

The salt of the organic phosphoric acid represented by Formula (2) is not particularly limited. For example, the salt may be in the form of salt (that is, an alkali metal salt, an alkaline-earth metal salt, and an amine salt) described above for the salt of the organic phosphonic acid represented by Formula (1), and the preferred form of the salt is also the same.

The salt of the organic phosphonic acid represented by Formula (1) and the salt of the organic phosphoric acid represented by Formula (2) may be in the form of a mono-salt or a di-salt.

The image recording paper medium of the present invention contains the specific organic phosphorus compound. The specific organic phosphorus compound fills voids of the paper medium to enhance the hydrophobicity thereof, and thus the permeation of moisture is effectively blocked. Therefore, the image recording paper medium excellently prevents the deformation thereof. Furthermore, the specific organic phosphorus compound substantially does not influence the quality (a dot diameter or a degree of glossiness) of the image formed on the paper medium.

The image recording paper medium of the present invention preferably has a calcium carbonate-containing coat layer as a surface layer, and the coat layer preferably contains the specific organic phosphorus compound. More specifically, the image recording paper medium of the present invention preferably has a pulp layer and a calcium carbonate-containing coat layer formed on the surface of the pulp layer, and the coat layer preferably contains the specific organic phosphorus compound. When the calcium carbonate-containing coat layer constituting the surface layer of the paper medium contains the specific organic phosphorus compound, the specific organic phosphorus compound interacts with the calcium carbonate, and thus the coat layer is appropriately hydrophobized. Accordingly, it is possible to effectively prevent moisture from permeating into the paper medium at the time of forming an image by applying an aqueous ink onto the surface of the coat layer. Furthermore, the specific organic phosphorus compound substantially does not influence the quality (a dot diameter or a degree of glossiness) of the image formed on the paper medium.

The calcium carbonate-containing coat layer may further contain kaolin, an organic polymer (preferably styrene-butadiene rubber), and the like. The content of the calcium carbonate in the calcium carbonate-containing coat layer is generally 50% by mass to 90% by mass, preferably 55% by mass to 80% by mass, and more preferably 60% by mass to 75% by mass.

In the present specification, "the coat layer contains (has) a specific organic phosphate compound" not only means a state where the specific organic phosphate compound is contained in the coat layer but also means a state where the specific organic phosphate compound is contained in and on the coat layer. Particularly, the state where the specific organic phosphate compound is contained in the coat layer is preferable. Herein, "the specific organic phosphate compound is contained on the coat layer" means a state where the specific organic phosphate compound is present on the surface of the coat layer (the surface on the image forming side). The state where "the coat layer contains (has) a specific organic phosphate compound" is not particularly limited as long as the coat layer contains the specific organic phosphate compound. For example, the specific organic phosphate compound may also be present in a layer (such as a pulp layer) other than the coat layer.

When the image recording paper medium of the present invention has the calcium carbonate-containing coat layer, and the coat layer contains the specific organic phosphorus compound, in order to cause appropriate interaction as intended, the content of the specific organic phosphorus compound contained in the coat layer is preferably 1 part by mass to 30 parts by mass, more preferably 2 parts by mass to 25 parts by mass, and even more preferably 4 parts by mass to 20 parts by mass, with respect to 100 parts by mass of the content of the calcium carbonate contained in the coat layer. In the present invention, "the content of the specific organic phosphorus compound contained in the coat layer" means the total content of the specific organic phosphorus compound contained in the coat layer.

It is preferable that the calcium carbonate and the specific organic phosphorus compound are homogenously present within the entire plane parallel to the surface of the coat layer. From the viewpoint of the degree of glossiness, the content of the specific organic phosphorus compound in the calcium carbonate-containing coat layer is preferably equal to or less than 10 g/m$^2$ with respect to the surface of the coat layer. Considering moisture barrier properties, the content of the specific organic phosphorus compound in the calcium carbonate-containing coat layer is more preferably 0.1 g/m$^2$ to 8.8 g/m$^2$, even more preferably 0.2 g/m$^2$ to 5.2 g/m$^2$, even more preferably 0.3 g/m$^2$ to 3.6 g/m$^2$, even more preferably 0.4 g/m$^2$ to 2.4 g/m$^2$, and still even more preferably 0.5 g/m$^2$ to 1.8 g/m$^2$.

[Manufacturing Image Recording Paper Medium]

The image recording paper medium of the present invention can be manufactured by adding the specific organic phosphorus compound to a paper medium which is generally used for forming an image. The method for adding the specific organic phosphorus compound to the paper medium is not particularly limited. However, generally, by coating the paper medium with a solution containing the specific organic phosphorus compound (hereinafter, also referred to as a "specific organic phosphorus compound solution"), it is possible to add the specific organic phosphorus compound to at least the surface layer of the paper medium that is coated with the solution.

<Paper Medium>

For manufacturing the image recording paper medium of the present invention, as the paper medium used as a raw material, commercially available general paper media can be used. Examples of thereof include fine paper (A) such as "OK Prince Fine" manufactured by Oji Paper Co., Ltd., "Shiraoi" manufactured by NIPPON PAPER INDUSTRIES CO., LTD., and "New NIP Fine" manufactured by NIPPON PAPER INDUSTRIES CO., LTD., fine coated paper such as "Silverdia" manufactured by NIPPON PAPER INDUSTRIES CO., LTD., lightly coated paper such as "OK Everlight Coat" manufactured by Oji Paper Co., Ltd. and "Aurora S" manufactured by NIPPON PAPER INDUSTRIES CO., LTD., lightweight coated paper (A3) such as "OK Coat L" manufactured by Oji Paper Co., Ltd. and "Aurora L" manufactured by NIPPON PAPER INDUSTRIES CO., LTD., coated paper (A2, B2) such as "OK Topcoat+" manufactured by Oji Paper Co., Ltd. and "Aurora Coat" manufactured by NIPPON PAPER INDUSTRIES CO., LTD., art paper (A1) such as "OK Kinfuji+" manufactured by Oji Paper Co., Ltd. and "Tokubishi Art" manufactured by MITSUBISHI PAPER MILLS LIMITED, and the like. Furthermore, various exclusive paper for photograph for ink jet recording can also be used.

Among the above recording media, the aforementioned coated paper is preferable. The coated paper is obtained by forming a coat layer on the surface of base paper (pulp layer) such as fine paper or neutral paper, which is mainly composed of cellulose and generally has not undergone surface treatment, by coating the surface with a coating material. It is particularly preferable to use coated paper in which a calcium carbonate-containing coat layer is formed on the pulp layer. Furthermore, it is preferable to use coated paper having a coat layer containing kaolin and the calcium carbonate on the pulp layer. More specifically, art paper, coated paper, lightweight coated paper, or lightly coated paper is more preferable.

From the viewpoint of a strong effect of inhibiting the migration of coloring materials and from the viewpoint of obtaining a high-quality image which has excellent color density and hue better than those of the related art, a water absorption coefficient Ka of the above recording media is preferably 0.05 mL/m$^2 \cdot$ms$^{1/2}$ to 0.5 mL/m$^2 \cdot$ms$^{1/2}$, more preferably 0.1 mL/m$^2 \cdot$ms$^{1/2}$ to 0.4 mL/m$^2 \cdot$ms$^{1/2}$, and even more preferably 0.2 mL/m$^2 \cdot$ms$^{1/2}$ to 0.3 mL/m$^2 \cdot$ms$^{1/2}$.

The water absorption coefficient Ka has the same definition as the absorption coefficient described in JAPAN TAPPI paper pulp test method No. 51:2000 (published from Japan Tappi.). Specifically, by using an automatic scanning liquid absorptometer KM500Win (manufactured by KUMAGAI RIKI KOGYO Co., Ltd.), the amounts of water transferred are measured at a contact time of 100 ms and a contact time of 900 ms, and from a difference therebetween, the water absorption coefficient Ka is calculated.

<Coating Paper Medium with Specific Organic Phosphorus Compound Solution>

The method for coating the paper medium with the specific organic phosphorus compound solution is not particularly limited, and a known liquid coating method can be used without particular limitation. For example, it is possible to adopt a wide variety of methods such as an ink jet method, a spray coating method, a roller coating method, and a dipping method.

Specific examples of the coating method of the specific organic phosphorus compound solution include a size press method represented by a horizontal size press method, a roll coater method, a calendar size press method, or the like; a size press method represented by an air knife coater method or the like; a knife coater method represented by an air knife coater method or the like; a roll coater method represented by a transfer roll coater method such as gate roll coater method, a direct roll coater method, a reverse roll coater method, a squeeze roll coater method, or the like; a buil blade coater method; a short dwell coater method; a blade coater method represented by a two stream coater method or the like; a bar coater method represented by a rod bar coater method or the like; a cast coater method; a gravure coater method; a curtain coater method; a die coater method, a brush coater method; a transfer method; and the like.

Furthermore, a method may be used in which the coating amount is controlled by using a coating device that includes a liquid amount restricting member just like the coating device described in JP1998-230201A (JP-H10-230201A).

The specific organic phosphorus compound solution may coat the paper medium by full coating in which the entirety of the paper medium is coated or by partial coating in which the paper medium is partially coated in an area that is coated with an ink by an ink coating step.

From the viewpoint of the degree of glossiness, it is preferable that the paper medium is coated with the specific organic phosphorus compound solution such that the amount of the specific organic phosphorus compound becomes equal to or less than 10 g/m$^2$. The paper medium is coated with the specific organic phosphorus compound solution such that the amount of the specific organic phosphorus compound more preferably becomes 0.1 g/m$^2$ to 8.8 g/m$^2$, even more preferably becomes 0.2 g/m$^2$ to 5.2 g/m$^2$, still more preferably becomes 0.3 g/m$^2$ to 3.6 g/m$^2$, yet more preferably becomes 0.4 g/m$^2$ to 2.4 g/m$^2$, and much more preferably becomes 0.5 g/m$^2$ to 1.8 g/m$^2$. Herein, "the paper medium is coated such that the amount of the specific organic phosphorus compound becomes equal to or less than 10 g/m$^2$" means that the paper medium is coated such that the total amount of the specific organic phosphorus compound becomes equal to or less than 10 g/m$^2$.

In order that the amount of the specific organic phosphorus compound in the paper medium falls into the aforementioned preferred range, the concentration of the specific organic phosphorus compound in the specific organic phosphorus compound solution is preferably 1% by mass to 50% by mass, more preferably 3% by mass to 40% by mass, and even more preferably 4% by mass to 30% by mass.

As a solvent of the specific organic phosphorus compound solution, any solvent can be used without particular limitation as long as it can dissolve the specific organic phosphorus compound. For example, it is possible to use an alcohol (preferably methanol, ethanol, 1-propanol, isopropanol, 1-butanol, or ethylene glycol), an amide-based solvent (preferably N,N-dimethylformamide, N,N-dimethylacetamide, or N-methyl-1-pyrrolidone), or a solvent mixture consisting of these. From the viewpoint of solubility, drying properties, and versatility, it is preferable to use an alcohol. Particularly, it is more preferable to use isopropanol, ethanol, 1-propanol, or 1-butanol.

From the viewpoint of coating suitability, at a temperature of 25° C., the viscosity of the specific organic phosphorus compound solution is preferably 0.1 mPa·s to 10 mPa·s, and more preferably 0.3 mPa·s to 50 mPa·s. The viscosity is measured based on JIS Z8803.

The specific organic phosphorus compound solution may contain a surfactant, a anti-foaming agent, a low-molecular weight organic acid, a pH adjuster, a viscosity adjuster, a preservative, a corrosion inhibitor, and the like, in addition to the specific organic phosphorus compound.

Generally, the paper medium coated with the specific organic phosphorus compound solution is subjected to a drying treatment. The drying treatment is not particularly limited. For example, it is possible to adopt heating treatment (performed at a temperature of 40° C. to 250° C., preferably at a temperature of 50° C. to 200° C., and more preferably at a temperature of 60° C. to 150° C.), a blasting treatment (such as exposing the paper medium to dry air), or the like.

When the calcium carbonate-containing coat layer of the image recording paper medium of the present invention contains the specific organic phosphorus compound, the image recording paper medium can be manufactured by coating the calcium carbonate-containing coat layer of the paper medium used as a raw material with the specific organic phosphorus compound solution.

In this case, from the viewpoint of causing an appropriate interaction between the calcium carbonate and the specific organic phosphorus compound as intended and from the viewpoint of suppressing the influence exerted on the image quality as much as possible, it is preferable to coat the coat layer with the specific organic phosphorus compound solution, such that the amount of the organic phosphorus compound coating the coat layer becomes 1 part by mass to 30 parts by mass (preferably 2 parts by mass to 25 parts by mass and more preferably 4 parts by mass to 20 parts by mass) with respect to 100 parts by mass of the content of the calcium carbonate contained in the coat layer.

The image recording paper medium of the present invention is not easily permeated by moisture when an image is formed thereon by using an aqueous ink and is effectively prevented from being deformed (curled) by the application of the aqueous ink. Furthermore, an image formed on the image recording paper medium of the present invention substantially does not experience a change in a degree of glossiness, in contrast to an image formed on the paper medium used as a raw material. In addition, when an image is formed on the image recording paper medium of the present invention by an ink jet method, the image substantially does not experience a change in a dot diameter, in contrast to an image formed on the paper medium used as a raw material by an ink jet method. That is, by using the image recording paper medium of the present invention, it is possible to excellently prevent the deformation of the paper medium while inhibiting the change of the image characteristics (a degree of glossiness and resolution) and to form a high-quality image.

[Image Recording Method]

The image recording method of the present invention includes the following steps (a) and (b).

(a) A step of coating a paper medium with the specific organic phosphorus compound solution (b) A step of forming an image by ejecting an aqueous ink by an ink jet method onto the surface of the paper medium that is coated with the specific organic phosphorus compound solution.

The paper medium used in the step (a) has the same definition as the paper medium used as a raw material for manufacturing the image recording paper medium of the present invention, and the preferred embodiment thereof is also the same.

In the step (a), as the method for coating the paper medium with the specific organic phosphorus compound solution, it is possible to adopt the same one as the method for coating the paper medium with the specific organic phosphorus compound solution for manufacturing the image recording paper medium of the present invention.

The image recording method of the present invention may include a step of drying the specific organic phosphorus compound solution coating the paper medium, between the step (a) and the step (b). As the drying step, it is possible to adopt the same one as the drying treatment for the paper medium coated with the specific organic phosphorus compound solution for manufacturing the image recording paper medium of the present invention.

The image recording method of the present invention preferably also includes a step of forming an organic acid-containing layer (hereinafter, also referred to as an "aggregation-inducing layer") between the step (a) and the step (b) (between the drying step and the step (b) if the image recording method includes the aforementioned drying step). The aggregation-inducing layer acts on the aqueous ink applied thereonto so as to cause aggregation of ink components such as a pigment. In this way, the aggregation-inducing layer enables the image formed of the aqueous ink to be fixed onto the paper medium.

The aggregation-inducing layer can be formed by coating the surface of the paper medium that is coated with the specific organic phosphorus compound solution with an organic acid-containing solution (hereinafter, also referred to as an "organic acid solution") and subjecting the organic acid solution to drying treatment if necessary. As such a coating method, it is possible to adopt the same one as the method for coating the paper medium with the specific organic phosphorus compound solution. As the drying treatment, it is possible to adopt the same one as the drying treatment for the paper medium coated with the specific organic phosphorus compound solution for manufacturing the image recording paper medium of the present invention described above.

The organic acid solution is generally an aqueous solution.

<Organic Acid>

The organic acid used for forming the aggregation-inducing layer is a compound which induces the aggregation (fixation) of the components in the aqueous ink by coming into contact with the aqueous ink on the paper medium. That is, the organic acid functions as a fixing agent.

Examples of the organic acid include polyacrylic acid, acetic acid, glycolic acid, malonic acid, malic acid, maleic acid, ascorbic acid, succinic acid, glutaric acid, fumaric acid, citric acid, tartaric acid, lactic acid, pyrrolidone carboxylic acid, pyrone carboxylic acid, pyrrole carboxylic acid, furan carboxylic acid, pyridine carboxylic acid, coumaric acid, thiophene carboxylic acid, nicotinic acid, oxalic acid, benzoic acid, and a phosphate compound. From the viewpoint of accomplishing both the inhibition of volatilization and the solubility in a solvent, the organic acid is preferably an acid having a molecular weight of equal to or greater than 35 and equal to or less than 1,000, more preferably an acid having a molecular weight of equal to or greater than 50 and equal to or less than 500, and particularly preferably an acid having a molecular weight of equal to or greater than 50 and equal to or less than 200. Furthermore, from the viewpoint of accomplishing both the prevention of blurring of ink and photocuring properties of the ink, the organic acid is preferably an acid having a pKa (in $H_2O$ at 25° C.) of equal to or greater than −10 and equal to or less than 7, more preferably an acid having a pKa of equal to or greater than 1 and equal to or less than 7, and particularly preferably an acid having a pKa of equal to or greater than 1 and equal to or less than 5.

As the pKa, it is possible to use values calculated by Advanced Chemistry Development (ACD/Labs) Software V11. 02 (1994-2014 ACD/Labs) or values described in documents (such as J. Phys. Chem. A 2011, 115, 6641 to 6645).

As the organic acid used in the present invention, an acidic compound having high water solubility is preferable. From the viewpoint of fixing the entirety of the ink by reacting with the ink components, the organic acid is preferably an acidic compound having three or less hydrogen atoms, and particularly preferably an acidic compound having two or three hydrogen atoms.

The organic acid is preferably one kind of compound or two or more kinds of compounds selected from DL-malic acid, malonic acid, glutaric acid, maleic acid, and a phosphate compound, and more preferably a combination of malonic acid and malic acid.

As the phosphate compound, an inorganic phosphate compound selected from orthophosphoric acid (hereinafter, simply referred to as "phosphoric acid"), phosphorous acid, hypophosphorous acid, pyrophosphoric acid, metaphosphoric acid, polyphosphoric acid, and a salt of these is preferable.

The content of the organic acid in the organic acid solution is preferably equal to or less than 40% by mass, more preferably 15% by mass to 40% by mass, even more preferably 15% by mass to 35% by mass, and particularly preferably 20% by mass to 30% by mass. If the content of the organic acid in the organic acid solution is within the aforementioned preferred range, the components in the ink can be efficiently fixed.

From the viewpoint of facilitating the aggregation of the ink composition, the pH of the organic acid solution is preferably 0.1 to 6.0 and more preferably 0.5 to 5.0 at a temperature of 25° C.

Furthermore, from the viewpoint of coating properties, at a temperature of 25° C., the viscosity of the organic acid solution is preferably 0.1 mPa·s to 100 mPa·s, and more preferably 0.5 mPa·s to 80 mPa·s. The viscosity can be measured by the same method as the method for measuring the viscosity of the aforementioned specific organic phosphorus compound solution.

The amount of the organic acid solution coating the paper medium coated with the specific organic phosphorus compound solution is not particularly limited as long as the amount is enough for causing the aggregation of the aqueous ink. However, from the viewpoint of facilitating the fixing of the aqueous ink, the paper medium is coated with the organic acid solution such that the amount of the organic acid coating the paper medium preferably becomes 0.1 $g/m^2$ to 2.0 $g/m^2$ and more preferably becomes 0.2 $g/m^2$ to 1.5 $g/m^2$.

The organic acid solution may further contain an aqueous organic solvent or a surfactant, in addition to the organic acid and water. Furthermore, the organic acid solution may contain known additives such as an ultraviolet absorber, a fading inhibitor, an antifungal agent, a pH adjuster, a corrosion inhibitor, an antioxidant, an emulsion stabilizer, a preservative, a anti-foaming agent, a viscosity adjuster, a dispersion stabilizer, and a chelating agent.

Next, the step (b) will be described.

In the step (b), an image is formed by ejecting an aqueous onto the aggregation-inducing layer by an ink jet method.

<Aqueous Ink>

The aqueous ink used in the present invention contains at least a colorant and water, and generally further contains a water-soluble organic solvent. The aqueous ink used in the present invention is in the form of a composition in which the respective components are homogeneously mixed together.

The aqueous ink (hereinafter, simply referred to as an "ink" in some cases) used in the present invention can be used not only for forming a monochromatic image, but also for forming a polychromatic image (such as a full color image). An image can be formed by selecting the aqueous ink with one intended color or selecting the aqueous inks with two or more intended colors. For forming a full color image, for example, as the inks, it is possible to use inks with magenta tone, cyan tone, and yellow tone can be used. Furthermore, an ink with black tone may also be used.

The aqueous ink used in the present invention may be an ink with yellow (Y) tone, magenta (M) tone, cyan (C) tone, block (K) tone, red (R) tone, green (G) tone, blue (B) tone, or white (W) tone, or may be a so-called special color ink in the field of printing.

The aqueous ink with each color tone described above can be prepared by changing the color of the colorant as intended.

(Colorant)

In the aqueous ink used in the present invention, a known dye, pigment, or the like can be used as a colorant without particular limitation. From the viewpoint of the coloring properties of the formed image, a colorant is preferable which substantially does not dissolve in water or poorly dissolves in water. Specific examples thereof include various pigments, disperse dyes, oil-soluble dyes, coloring agents forming an J-aggregate, and the like. Considering light fastness, the colorant is more preferably a pigment.

The type of the pigment that can be contained in the aqueous ink used in the present invention is not particularly limited, and general organic or inorganic pigments can be used.

Examples of the organic pigments include an azo pigment, a polycyclic pigment, a dye chelate, a nitro pigment, a nitroso pigment, aniline black, and the like. Among these, an azo pigment or a polycyclic pigment is more preferable. Examples of the azo pigment include azo lake, an insoluble azo pigment, a condensed azo pigment, and a chelate azo pigment. Examples of the polycyclic pigment include a phthalocyanine pigment, a perylene pigment, a perinone pigment, an anthraquinone pigment, a quinacridone pigment, a dioxazine pigment, an indigo pigment, a thioindigo pigment, an isoindolinone pigment, and a quinophthalone pigment. Examples of the dye chelate include a basic dye chelate and an acidic dye chelate.

Examples of the inorganic pigments include titanium oxide, iron oxide, calcium carbonate, barium sulfate, aluminum hydroxide, barium yellow, cadmium red, chromium yellow, carbon black, and the like. Among these, carbon black is preferable. Examples of the carbon black include those manufactured by a known method such as a contact method, a furnace method, or a thermal method.

Specific examples of the pigments that can be used in the present invention include the pigments described in paragraphs "0142" to "0145" in JP2007-100071A and the like.

When a dye is used as a coloring component in the present invention, a dye supported on a water-insoluble support can be used as a colorant. Known dyes can be used as the dye without particular limitation. For example, in the present invention, the dyes described in JP2001-115066A, JP2001-335714A, JP2002-249677A, and the like can also be preferably used. Furthermore, the support is not particularly limited as long as it is insoluble or poorly soluble in water. As the support, an inorganic material, an organic material, or a composite material of these can be used. Specifically, in the present invention, the supports described in JP2001-181549A, JP2007-169418A, and the like can also be preferably used.

The support (colorant) supporting a dye can be used as is. Alternatively, if necessary, it can be used concurrently with a dispersant. As the dispersant, a dispersant which will be described later can be preferably used.

One kind of the colorant may be used singly, or plural kinds thereof may be selected and used in combination.

From the viewpoint of the color density, the graininess, the stability of the ink, and the ejection reliability, the content of the colorant in the aqueous ink used in the present invention is preferably 1% by mass to 35% by mass and more preferably 1% by mass to 25% by mass, with respect to the total mass of the aqueous ink.

(Dispersant)

When the aqueous ink used in the present invention is an aqueous ink, and the colorant is a pigment, it is preferable that the pigment constitutes coloring particles dispersed in an aqueous solvent by a dispersant (hereinafter, simply referred to as "coloring particles").

The dispersant may be a polymer dispersant or a low-molecular weight surfactant-type dispersant. Furthermore, the polymer dispersant may be either a water-soluble polymer dispersant or a water-insoluble polymer dispersant.

As the low-molecular weight surfactant-type dispersant, for example, known low-molecular weight surfactant-type dispersants described in paragraphs "0047" to "0052" of JP2011-178029A can be used.

Examples of the water-soluble dispersant among the polymer dispersants include a hydrophilic polymer compound. Examples of a natural hydrophilic polymer compound include a vegetable polymer such as gum Arabic, gum tragacanth, guar gum, karaya gum, locust bean gum, arabinogalactone, pectin, or quince seed starch, a seaweed-based polymer such as alginic acid, carrageenan, or agar, an animal polymer such as gelatin, casein, albumin, or collagen, a microorganism-based polymer such as xanthan gum or dextrin, and the like.

Examples of a modified hydrophilic polymer compound using a natural substance as a raw material include a cellulose-based polymer such as methylcellulose, ethylcellulose, hydroxyethyl cellulose, hydroxypropyl cellulose, or carboxymethyl cellulose, a starch-based polymer such as sodium starch glycolate or sodium starch phosphoric acid ester, a seaweed-based polymer such as sodium alginate or propylene glycol alginic acid ester, and the like.

Examples of a synthesized hydrophilic polymer compound include a vinyl-based polymer such as polyvinyl alcohol, polyvinylpyrrolidone, or polyvinyl methyl ether, an acrylic resin such as non-crosslinked polyacrylamide, polyacrylic acid or an alkali metal salt thereof, or a water-soluble styrene acrylic resin, a water-soluble styrene-maleic acid resin, a water-soluble vinylnaphthalene acrylic resin, a water-soluble vinylnaphthalene-maleic acid resin, a polymer compound having a salt of a cationic functional group such as polyvinylpyrrolidone, polyvinyl alcohol, an alkali metal salt of β-naphthalene sulfonate formalin condensate, quaternary ammonium, or an amino group on a side chain thereof, a natural polymer compound such as shellac, and the like.

Among the above polymers, a hydrophilic polymer compound into which a carboxyl group is introduced, such as a homopolymer of acrylic acid or methacrylic acid or a copolymer of acrylic acid or methacrylic acid with other monomers, is preferable.

The water-insoluble polymer dispersant is not particularly limited as long as it is a water-insoluble polymer and can disperse a pigment, and a water-insoluble polymer dispersant known in the related art can be used. For example, the water-insoluble polymer dispersant can be constituted with both a hydrophobic structural unit and a hydrophilic structural unit.

Examples of the monomer component constituting the hydrophobic structural unit include a styrene-based monomer component, an alkyl (meth)acrylate component, an aromatic group-containing (meth)acrylate component, and the like.

The monomer component constituting the hydrophilic structural unit is not particularly limited as long as it is a monomer component containing a hydrophilic group. Examples of the hydrophilic group include a nonionic group, a carboxyl group, a sulfonic acid group, a phosphoric acid group, and the like. Examples of the nonionic group include a hydroxyl group, an amide group (having an unsubstituted nitrogen atom), a group derived from an alkylene oxide polymer (such as polyethylene oxide or polypropylene oxide), a group derived from sugar alcohol, and the like.

From the viewpoint of the dispersion stability, the hydrophilic structural unit preferably contains at least a carboxyl group. It is also preferable that the hydrophilic structural unit contains both the nonionic group and the carboxyl group.

Specific examples of the water-insoluble polymer dispersant include a styrene-(meth)acrylic acid copolymer, a styrene-(meth)acrylic acid-(meth)acrylic acid ester copolymer, a (meth)acrylic acid ester-(meth)acrylic acid copolymer, a polyethylene glycol (meth)acrylate-(meth)acrylic acid copolymer, a styrene-maleic acid copolymer, and the like.

From the viewpoint of the dispersion stability of the pigment, the water-insoluble polymer dispersant is preferably a vinyl polymer containing a carboxyl group, and more preferably a vinyl polymer having at least a structural unit derived from an aromatic group-containing monomer as the hydrophilic structural unit and a structural unit containing a carboxyl group as the hydrophilic structural unit.

From the viewpoint of the dispersion stability of the pigment, the weight average molecular weight of the water-insoluble polymer dispersant is preferably 3,000 to 200,000, more preferably 5,000 to 100,000, even more preferably 5,000 to 80,000, and particularly preferably 10,000 to 60,000.

In the present specification, the weight average molecular weight is measured by gel permeation chromatography (GPC). GPC is performed by using HLC-8220 GPC (manufactured by TOSOH CORPORATION) and using TSKgel Super HZM-H, TSKgel Super HZ4000, and TSKgel Super HZ2000 (manufactured by TOSOH CORPORATION, 4.6 mmID×15 cm) as columns. The conditions of GPC are specifically described in paragraph "0076" of JP2010-155359A.

From the viewpoint of the dispersibility of the pigment, the coloring properties of the ink, and the dispersion stability, the content of the dispersant in the coloring particles is preferably 10 parts by mass to 90 parts by mass, more preferably 20 parts by mass to 70 parts by mass, and particularly preferably 30 parts by mass to 50 parts by mass, with respect to 100 parts by mass of the pigment.

It is preferable that the content of the dispersant in the coloring particles is within the above range, because then the pigment is coated with an appropriate amount of the dispersant, and coloring particles which have a small particles size and excellent temporal stability tend to be easily obtained.

For example, the coloring particles can be obtained in the form of a coloring particle dispersion by dispersing a mixture, which contains a pigment, a dispersant, and a solvent (preferably an organic solvent) used if necessary, and the like, by using a disperser.

For example, the coloring particle dispersion can be manufactured by performing a step (mixing•hydrating step) of adding a basic substance-containing aqueous solution to a mixture of the aforementioned pigment, the aforementioned polymer dispersant, and an organic solvent which dissolves or disperses the dispersant, and then performing a step (solvent removing step) of removing the organic solvent. In this way, the colorant is finely dispersed, and a dispersion of coloring particles having excellent preservation stability can be prepared.

The organic solvent needs to be able to dissolve or disperse the dispersant. In addition to this, it is preferable that the organic solvent exhibits affinity with water to some extent. Specifically, at a temperature of 20° C., the degree of solubility of the organic solvent in water is preferably 10% by mass to 50% by mass.

Preferred examples of the organic solvent include water-soluble organic solvents. Among these, isopropanol, acetone, and methyl ethyl ketone are preferable, and methyl ethyl ketone is particularly preferable. One kind of the organic solvent may be used singly, or plural kinds thereof may be used concurrently.

The aforementioned basic substance is used for neutralizing an anionic group (preferably a carboxyl group) that the polymer has in some cases. A degree of neutralization of the anionic group is not particularly limited. Generally, the finally obtained coloring particle dispersion preferably has properties in which the pH thereof is 4.5 to 10, for example. The pH can be determined by an intended degree of neutralization of the aforementioned polymer.

In the process of manufacturing the coloring particle dispersion, the method for removing the organic solvent is not particularly limited, and a known method such as distillation under reduced pressure can be used.

In the aqueous ink used in the present invention, one kind of the coloring particles may be used singly, or two or more kinds thereof may be used in combination.

In the present invention, the volume average particle size of the colorant (or the coloring particles) is preferably 10 nm to 200 nm, more preferably 10 nm to 150 nm, and even more preferably 10 nm to 100 nm. If the volume average particle size is equal to or less than 200 nm, color reproducibility become excellent, and droplet ejection characteristics become excellent in the case of an ink jet method. If the volume average particle size is equal to or greater than 10 nm, light fastness becomes excellent.

The particle size distribution of the colorant (or the coloring particles) is not particularly limited, and may be wide particle size distribution or monodisperse particle size distribution. Furthermore, two or more kinds of colorants having monodisperse particle size distribution may be used by being mixed together.

The volume average particle size of the colorant (or the coloring particles) can be measured by using a Microtrac particle size distribution analyzer (trade name: Version 10. 1. 2-211BH, manufactured by NIKKISO CO., LTD.) by means of a dynamic light scattering method.

(Solvent)

The aqueous ink used in the present invention contains water as a solvent and generally further contains a water-soluble organic solvent. The content of water in the solvent contained in the aqueous ink is preferably equal to or greater than 10% by mass, more preferably 20% by mass to 100% by mass, even more preferably 30% by mass to 90% by mass, and still more preferably 40% by mass to 80% by mass.

The water-soluble organic solvent which can be contained in the aqueous ink preferably has a degree of solubility in water of equal to or greater than 0.1% by mass at a temperature of 20° C. Examples of the water-soluble organic solvent include an alcohol, ketone, an ether compound, an amide compound, a nitrile compound, and a sulfone compound.

The alcohol is not particularly limited, and examples thereof include ethanol, isopropanol, n-butanol, t-butanol, isobutanol, diacetone alcohol, diethylene glycol, ethylene glycol, dipropylene glycol, propylene glycol, and glycerin.

The ketone is not particularly limited, and examples thereof include acetone, methyl ethyl ketone, diethyl ketone, and methyl isobutyl ketone.

The ether compound is not particularly limited, and examples thereof include dibutyl ether, tetrahydrofuran, dioxane, and tripropylene glycol monomethyl ether.

The amide compound is not particularly limited, and examples thereof include dimethylformamide and diethylformamide.

The nitrile compound is not particularly limited, and examples thereof include acetonitrile.

The sulfone compound is not particularly limited, and examples thereof include dimethyl sulfoxide, dimethyl sulfone, and sulfolane.

(Resin Particles)

If necessary, the aqueous ink used in the present invention can contain resin particles.

It is preferable that the resin particles have a function of fixing the ink by thickening the ink by being unstably dispersed and aggregated when coming into contact with the aforementioned aggregation-inducing layer. It is preferable that such resin particles are dispersed in at least one of the water and organic solvent.

As the resin particles, it is possible to use an acrylic resin, a vinyl acetate-based resin, a styrene-butadiene-based resin, a vinyl chloride-based resin, an acryl-styrene-based resin, a butadiene-based resin, a styrene-based resin, a crosslinked acrylic resin, a crosslinked styrene-based resin, a benzoguanamine resin, a phenolic resin, a silicone resin, an epoxy resin, a urethane-based resin, a paraffin-based resin, a fluorine-based resin, or latex of these. Among these, an acrylic resin, an acryl-styrene-based resin, a styrene-based resin, a crosslinked acrylic resin, and a crosslinked styrene-based resin are preferable, for example.

It is also possible to use the resin particles in the form of latex.

The weight average molecular weight of the polymer constituting the resin particles is preferably equal to or greater than 10,000 and equal to or less than 200,000, and more preferably equal to or greater than 20,000 and equal to or less than 200,000.

The volume average particle size of the resin particles is preferably within a range of 1 nm to 1 μm, more preferably within a range of 1 nm to 200 nm, even more preferably within a range of 2 nm to 100 nm, and particularly preferably within a range of 5 nm to 50 nm. The volume average particle size of the resin particles can be measured by the same method as used for measuring the volume average particle size of the aforementioned colorant.

A glass transition temperature Tg of the resin particles is preferably equal to or higher than 30° C., more preferably equal to or higher than 40° C., and even more preferably equal to or higher than 50° C.

Tg can be measured by using a differential scanning calorimeter (DSC) EXSTAR 6220 manufactured by SII NanoTechnology, Inc at a temperature increase rate of 10° C./min. At this time, the average of a temperature, at which a base line starts to change as the resin particles undergo transition to glass, and a temperature that returns to the base line is determined as Tg.

As the resin particles, it is preferable to use self-dispersing resin particles.

The self-dispersing resin particles refer to a water-insoluble resin which can be in a dispersed state in an aqueous medium by a functional group (particularly, an acidic group or a salt thereof) contained in the polymer when the polymer is put into a dispersed state by a phase-inversion emulsification method in the absence of a surfactant.

Herein, the dispersed state includes both of an emulsified state (emulsion) in which the water-insoluble resin is dispersed in a liquid state in an aqueous medium and a dispersed state (dispersion) in which the water-insoluble resin is dispersed in a solid state in an aqueous medium.

As the self-dispersing resin particles, it is possible to use the self-dispersing resin particles described in paragraphs "0090" to "0121" of JP2010-64480A and in paragraphs "0130" to "0167" of JP2011-068085A.

The molecular weight of the water-insoluble polymer constituting the self-dispersing resin particles is preferably 3,000 to 200,000, more preferably 5,000 to 150,000, and even more preferably 10,000 to 100,000, in terms of a weight average molecular weight. By setting the weight average molecular weight to be equal to or greater than 3,000, the amount of water-soluble components can be effectively reduced. Furthermore, by setting the weight average molecular weight to be equal to or less than 200,000, the self-dispersion stability can be improved.

From the viewpoint of controlling the hydrophilicity and hydrophobicity of the polymer, the water-insoluble polymer constituting the resin particles preferably contain a structural unit derived from an aromatic group-containing (meth)acrylate monomer (preferably a structural unit derived from phenoxyethyl (meth)acrylate and/or a structural unit derived from benzyl (meth)acrylate) in an amount of 15% by mass to 80% by mass in terms of a copolymerization ratio, with respect to the total mass of the resin particles.

Furthermore, from the viewpoint of controlling the hydrophilicity and hydrophobicity of the polymer, the water-insoluble polymer preferably contains a structural unit derived from an aromatic group-containing (meth)acrylate monomer in an amount of 15% by mass to 80% by mass in terms of a copolymerization ratio, a structural unit derived from a carboxyl group-containing monomer, and a structural unit derived from an alkyl group-containing monomer (preferably a structural unit derived from an alkyl ester of (meth)acrylic acid), more preferably contains a structural unit derived from phenoxyethyl (meth)acrylate and/or a structural unit derived from benzyl (meth)acrylate in an amount of 15% by mass to 80% by mass in terms of a copolymerization ratio, a structural unit derived from a carboxyl group-containing monomer, and a structural unit derived from an alkyl group-containing monomer (preferably a structural unit derived from an alkyl ester of (meth)acrylic acid having 1 to 4 carbon atoms). In addition, the water-insoluble polymer preferably has an acid value of 25 to 100 and a weight average molecular weight of 3,000 to 200,000, and more preferably has an acid value of 25 to 95 and a weight average molecular weight of 5,000 to 150,000.

The content of the resin particles is preferably 0.1% by mass to 20% by mass and more preferably 0.1% by mass to 10% by mass, with respect to the total mass of the aqueous ink.

The particle size distribution of the resin particles is not particularly limited, and may be wide particle size distribution or monodisperse particle size distribution. Furthermore, two or more kinds of resin particles having monodisperse particle size distribution may be used by being mixed together.

(Surfactant)

The aqueous ink used in the present invention may contain a surfactant as a surface tension adjuster.

As the surfactant, it is possible to use any of an anionic surfactant, a cationic surfactant, an amphoteric surfactant, a nonionic surfactant, and a betaine-based surfactant.

Specific examples of the anionic surfactant include sodium dodecylbenzenesulfonate, sodium lauryl sulfate, sodium alkyl diphenyl ether disulfonate, sodium alkyl naphthalene sulfonate, sodium dialkyl sulfosuccinate, sodium stearate, potassium oleate, sodium dioctylsulfosuccinate, sodium polyoxyethylene alkyl ether sulfate, sodium polyoxyethylene alkyl ether sulfate, sodium polyoxyethylene alkyl phenyl ether sulfate, sodium dialkyl sulfosuccinate, sodium stearate, sodium oleate, a sodium t-octylphenoxyethoxypolyethoxyethyl sulfate salt, and the like. One kind of surfactant or two or more kinds of surfactants can be selected from these.

Specific examples of the nonionic surfactant include acetylene diol derivative such as an ethylene oxide adduct of acetylene diol, polyoxyethylene lauryl ether, polyoxyethylene octylphenyl ether, polyoxyethylene oleyl phenyl ether, polyoxyethylene nonylphenyl ether, oxyethylene-oxypropylene block copolymer, t-octyl phenoxyethyl polyethoxy ethanol, nonyl phenoxyethyl polyethoxy ethanol, and the like. One kind of surfactant or two or more kinds of surfactants can be selected from these.

Examples of the cationic surfactant include a tetraalkyl ammonium salt, an alkyl amine salt, a benzalkonium salt, an alkylpyridium salt, an imidazolium salt, and the like. Specific examples thereof include dihydroxy ethyl stearylamine, 2-heptadecenyl-hydroxyethyl imidazoline, lauryl dimethyl benzyl ammonium chloride, cetylpyridinium chloride, stearamide methyl pyridium chloride, and the like.

Among these surfactants, from the viewpoint of the stability, a nonionic surfactant is preferable, and an acetylene diol derivative is more preferable.

When the aqueous ink used in the present invention is used in an ink jet recording method, from the viewpoint of ejection properties of the ink, the amount of the surfactant is preferably adjusted such that the surface tension of the aqueous ink becomes 20 mN/m to 60 mN/m, more preferably adjusted such that the surface tension becomes 20 mN/m to 45 mN/m, and more preferably adjusted such that the surface tension becomes 25 mN/m to 40 mN/m.

The surface tension of the aqueous ink is measured by using an Automatic Surface Tensiometer CBVP-Z (manufactured by Kyowa Interface Science Co., LTD.) at a temperature of 25° C.

The content of the surfactant in the aqueous ink is preferably an amount that enables the surface tension of the aqueous ink to fall into the aforementioned range. More specifically, the content of the surfactant in the aqueous ink is preferably equal to or greater than 0.1% by mass, more preferably 0.1% by mass to 10% by mass, and even more preferably 0.2% by mass to 3% by mass.

(Other Components)

If necessary, the aqueous ink used in the present invention may be mixed with additives such as a dehydration inhibitor (swelling agent), a desiccant, a coloration inhibitor, a penetration enhancer, an ultraviolet absorber, a preservative, a corrosion inhibitor, a anti-foaming agent, a viscosity adjuster, a pH adjuster, and a chelating agent. The mixing method is not particularly limited, and by appropriately selecting a generally used mixing method, the aqueous ink can be obtained.

(Physical Properties of Aqueous Ink)

The viscosity at a temperature of 25° C. of the aqueous ink used in the present invention is preferably equal to or greater than 1.2 mPa·s and equal to or less than 15.0 mPa·s, more preferably equal to or greater than 2 mPa·s and less than 13 mPa·s, and even more preferably equal to or greater than 2.5 mPa·s and less than 10 mPa·s.

The viscosity of the aqueous ink is measured by using a VISCOMETER TV-22 (manufactured by TOKI SANGYO CO., LTD.) at a temperature of 25° C.

From the viewpoint of the dispersion stability, at a temperature of 25° C., the pH of the aqueous ink used in the present invention is preferably 6 to 11, more preferably 7 to 10, and even more preferably 7 to 9.

<Image Formation>

By coating the aggregation-inducing layer with the aqueous ink, an intended image can be formed. In the present invention, the aqueous ink is ejected onto the aggregation-inducing layer by an ink jet method.

As the recording method using the ink jet method preferable in the present invention, it is possible to adopt the method described in paragraphs "0093" to "0105" of JP2003-306623A. Hereinafter, the ink jet method will be more specifically described.

(Ink Jet Method)

The ink jet method used for image recording of the present invention is not particularly limited, and a known method can be adopted. For example, the ink jet method may be any of a charge controlling method in which an ink is ejected by using electrostatic attraction force; a drop-on-demand method (a pressure pulse method) using vibration pressure of a piezoelectric element; an acoustic ink jet method in which an ink is irradiated with an acoustic beam converted from an electric signal and the ink is ejected by using the radiation pressure; and a thermal ink jet method in which air bubbles are formed by heating an ink and the thus generated pressure is used; and the like.

Furthermore, an ink jet head used in the ink jet method may be an on-demand type or a continuous type. In addition, an ink nozzle or the like used at the time of performing recording by the ink jet method is not particularly limited, and can be appropriately selected according to the purpose.

The ink jet method includes a method of ejecting a large number of low-concentration inks called photo inks in a small volume, a method of improving image quality by using a plurality of inks which have substantially the same color but different densities, and a method of using a colorless and transparent ink.

The ink jet method also includes a shuttle method of using a short serial head, in which recording is performed while a recording medium is being scanned in a width direction by the head, and a line method of using a line head in which recording elements are arranged to correspond to the entire region of one side of a recording medium. In the line method, the recording medium is scanned in a direction orthogonal to the arrangement direction of the recording elements, and accordingly, an image can be recorded on the entire surface of the recording medium, and a transport system such as a carriage scanning the short head is not required. Moreover, complicated scanning control for moving a carriage and a recording medium is not required, and only the recording medium is moved. Therefore, the recording speed in the line method can be increased to more than that in the shuttle method.

When an ink application step is performed by the ink jet method, from the viewpoint of forming a high-definition print, the amount of the aqueous ink droplets ejected by the ink jet method is preferably 1.5 pL to 3.0 pL, and more preferably 1.5 pL to 2.5 pL. The amount of the aqueous ink droplets ejected can be regulated by appropriately adjusting the ejection conditions.

(Ink Drying Step)

If necessary, the step (b) may include an ink drying step of drying and removing a solvent (such as water or the aforementioned aqueous medium) in the aqueous ink applied onto the aggregation-inducing layer. The ink drying step is not particularly limited as long as at least a portion of the solvent of the ink can be removed, and a generally used method can be adopted.

(Thermal Fixing Step)

If necessary, the step (b) preferably includes a thermal fixing step after the ink drying step. By performing the thermal fixing treatment, the image on the recording medium can be fixed, and the scratch resistance of the image can be further improved. As the thermal fixing step, for example, it is possible to adopt the thermal fixing step described in paragraphs "0112" to "0120" of JP2010-221415A.

(Ink Removing Step)

If necessary, the ink jet recording method of the present invention may include an ink removing step of removing the aqueous ink (such as solids of the ink solidified by drying) having adhered to the ink jet recording head by using a maintenance liquid. Specifically, as the maintenance liquid and the ink removing step, the maintenance liquid and the ink removing step described in WO2013/180074A can be preferably adopted.

EXAMPLES

Hereinafter, the present invention will be more specifically described based on examples, but the present invention is not limited to the examples. Herein, unless otherwise specified, "part" and "%" showing the composition are based on mass.

[Preparation of Specific Organic Phosphorus Compound Solution]

A specific organic phosphorus compound shown in the following table 2 was dissolved in isopropanol, thereby preparing a specific organic phosphorus compound solution with a concentration of 15.8% by mass. At a temperature of 25° C., the viscosity of the obtained solution was within a range of 0.3 mPa·s to 1.2 mPa·s.

[Preparation of Image Recording Paper Medium Containing Specific Organic Phosphorus Compound]

An A4 size paper medium shown in the following table 2 was fully coated with the specific organic phosphorus compound solution such that the amount of the specific organic phosphorus compound coating the paper medium became as shown in the following table 2 (in a paper medium having a coat layer, the coat layer was fully coated). Thereafter, the solution was dried for 10 minutes at a temperature of 80° C., thereby preparing an image recording paper medium containing the specific organic phosphorus compound.

In Comparative examples 1 to 4 shown in the following table 2, instead of the specific organic phosphorus compound, hexamethylene diisocyanate, Megafac F-511, and methylene diphosphonate were used.

<Measuring Ratio Between Calcium Carbonate Content and Specific Organic Phosphorus Compound Content Contained in Coat Layer>

In Examples and Comparative examples using coated paper as the aforementioned paper medium, the coat layer containing the specific organic phosphorus compound is peeled off from the coated paper with a razor and subjected to FT-IR spectroscopy by a KBr method. In this way, the peak intensity was analyzed, and a ratio between the calcium carbonate content and the specific organic phosphorus compound content contained in the coat layer was calculated.

[Formation of Aggregation-Inducing Layer]

An organic acid solution having the following composition was prepared.

| | |
|---|---|
| Malonic acid (manufactured by Wako Pure Chemical Industries, Ltd.) | . . . 11.3% |
| Malic acid (manufactured by Wako Pure Chemical Industries, Ltd.) | . . . 14.5% |
| DEGmBE (diethylene glycol monobutyl ether) | . . . 7.5% |
| TEGmME (triethylene glycol monomethyl ether) | . . . 2.5% |
| Deionized water | Balance |

At a temperature of 25° C., the pH and the viscosity of the obtained organic acid solution were 1.1 and 0.6 mPa·s respectively.

By using a bar coater, the image recording paper medium (the surface of the paper medium that was coated with the specific organic phosphorus compound solution) was fully coated with the organic acid solution prepared as above such that the amount of the organic acid coating the paper medium became 0.25 g/m$^2$. Thereafter, the organic acid solution was dried for 2 seconds at 50° C., thereby forming an aggregation-inducing layer.

[Preparation of Aqueous Ink]

<Synthesis of Polymer Dispersant P-1>

A polymer dispersant P-1 was synthesized as below.

88 g of methyl ethyl ketone was put into a 1,000 mL three-neck flask equipped with a stirrer and a cooling tube, and heated to 72° C. in a nitrogen atmosphere. To the resultant, a solution, which was obtained by dissolving 0.85 g of dimethyl 2,2'-azobisisobutyrate, 60 g of benzyl methacrylate, 10 g of methacrylic acid, and 30 g of methyl methacrylate in 50 g of methyl ethyl ketone, was added dropwise over 3 hours. After the dropwise addition ended, the resultant was further reacted for 1 hour. Thereafter, a solution, which was obtained by dissolving 0.42 g of dimethyl 2,2'-azobisisobutyrate in 2 g of methyl ethyl ketone, was added thereto, and the resultant was heated for 4 hours at 78° C. The obtained reaction solution was reprecipitated twice in a large excess of hexane, and the precipitated resin was dried, thereby obtaining 96 g of a polymer dispersant P-1.

The composition of the obtained polymer dispersant P-1 was confirmed by $^1$H-NMR. The polymer dispersant P-1 had a weight average molecular weight of 44,600. The polymer dispersant P-1 had an acid value of 1.16 mgKOH/g. The acid value was measured by the method described in JIS standard (JIS K 0070:1992).

<Preparation of Pigment Dispersion Liquid>

(Preparation of Cyan Dispersion)

10 parts of Pigment Blue 15:3 (phthalocyanine blue A220, manufactured by Dainichiseika Color & Chemicals Mfg. Co., Ltd.) as a cyan pigment, 5 parts of the polymer dispersant P-1, 42 parts of methyl ethyl ketone, 5.5 parts of an 1N aqueous NaOH solution, and 87.2 parts of deionized water were mixed together and dispersed for 2 to 6 hours by a beads mill using 0.1 mmφ zirconia beads.

From the obtained dispersion, methyl ethyl ketone was removed under reduced pressure at 55° C., and a portion of water was removed. Furthermore, by using a high-speed refrigerated centrifuge 7550 (manufactured by KUBOTA CORPORATION) and a 50 mL centrifuge tube, the dispersion was subjected to a centrifugation treatment for 30 minutes at 8,000 rpm, and the supernatant liquid other than the precipitate was collected.

Then, the pigment concentration was determined from the absorbance spectrum. A dispersion (cyan dispersion liquid C) of resin-coated pigment particles (pigment coated with the polymer dispersant) having a pigment concentration of 10.2% by mass was obtained. The volume average particle size of the pigment particles of the obtained cyan dispersion liquid C was 105 nm.

The volume average particle size was measured with a nanotrac particle size distribution analyzer UPA-EX150 (manufactured by NIKKISO CO., LTD.) by a dynamic light scattering method.

(Preparation of Magenta Dispersion Liquid)

A dispersion (magenta dispersion liquid M) of resin-coated pigment particles (pigment coated with the polymer dispersant) was prepared in the same manner as in the preparation of the cyan dispersion liquid, except that in the preparation of the cyan dispersion liquid, Pigment Red 122 as a magenta pigment was used instead of Pigment Blue 15:3 (phthalocyanine blue A220, manufactured by Dainichiseika Color & Chemicals Mfg Co., Ltd.). The volume average particle size of the obtained magenta dispersion liquid M was 85 nm.

(Preparation of Yellow Dispersion Liquid)

A dispersion (yellow dispersion liquid Y) of resin-coated pigment particles (pigment coated with the polymer dispersant) was prepared in the same manner as in the preparation of the cyan dispersion liquid, except that in the preparation of the cyan dispersion liquid, Pigment Yellow 74 as a yellow pigment was used instead of Pigment Blue 15:3 (phthalocyanine blue A220, manufactured by Dainichiseika Color & Chemicals Mfg Co., Ltd.). The volume average particle size of the obtained yellow dispersion liquid Y was 82 nm.

(Preparation of Black Dispersion Liquid)

A dispersion (black dispersion liquid K) of resin-coated pigment particles (pigment coated with the polymer dispersant) was prepared in the same manner as in the preparation of the cyan dispersion liquid, except that in the preparation of the cyan dispersion liquid, carbon black (NIPEX 160-IQ manufactured by Evonik Degussa Co., Ltd.) as a black pigment was used instead of Pigment Blue 15:3 (phthalocyanine blue A220, manufactured by Dainichiseika Color & Chemicals Mfg Co., Ltd.). The volume average particle size of the obtained black dispersion liquid K was 130 nm.

<Preparation of Self-Dispersing Resin Particles D-01>

A 2 L three-neck flask equipped with a stirrer, a thermometer, a reflux condenser tube, and a nitrogen gas inlet tube was filled with 360.0 g of methyl ethyl ketone and heated to 75° C. In a state where the internal temperature of the reaction container was kept at 75° C., a solution mixture composed of 180.0 g of phenoxyethyl acrylate, 162.0 g of methyl methacrylate, 18.0 g of acrylic acid, 72 g of methyl ethyl ketone, and 1.44 g of "V-601" (manufactured by Wako Pure Chemical Industries, Ltd.) was added dropwise thereto at a constant speed such that the dropwise addition was completed in 2 hours. After the dropwise addition was completed, a solution composed of 0.72 g of "V-601" and 36.0 g of methyl ethyl ketone was added thereto, and the resultant was stirred for 2 hours at 75° C. Then a solution composed of 0.72 g of "V-601" and 36.0 g of isopropanol was further added thereto, and the resultant was stirred for 2 hours at a temperature of 75° C. Thereafter, the resultant was heated to 85° C. and continuously stirred for two more hours. The obtained copolymer had a weight average molecular weight of 64,000 and an acid value of 0.69 mmol/g.

Subsequently, 668.3 g of the polymer solution was weighed out, 388.3 g of isopropanol and 145.7 ml of an 1 mol/L aqueous NaOH solution were added thereto, and the internal temperature of the reaction container was heated to 80° C. Then, 720.1 g of distilled water was added dropwise thereto at a rate of 20 ml/min such that the polymer was dispersed in water. Thereafter, under the atmospheric pressure, the resultant was kept for 2 hours at an internal temperature of the reaction container of 80° C., for 2 hours at an internal temperature of the reaction container of 85° C., and then for 2 hours at an internal temperature of the reaction container of 90° C. Then, the internal pressure of the reaction container was reduced, and a total of 913.7 g of isopropanol, methyl ethyl ketone, and distilled water were distilled away, thereby obtaining an aqueous dispersion (emulsion) of self-dispersing resin particles (D-01) having a concentration of solid contents of 28.0%.

<Preparation of Ink>

Each of the pigment dispersion liquids (the cyan dispersion liquid C, the magenta dispersion liquid M, the yellow dispersion liquid Y, and the black dispersion liquid K) and the self-dispersing rein particles D-01 obtained as above were mixed together such that the composition (unit: %) of an ink shown in the following table 1 was obtained, thereby preparing ink compositions.

Each of the prepared ink compositions was filtered through a PVDF 5 μm filter (Millex SV manufactured by Millipore Corporation, diameter: 25 mm) by using a plastic disposable syringe, thereby obtaining finished inks (a magenta ink M, a black ink K, a cyan ink C, and a yellow ink Y).

[Table 1]

TABLE 1

|  | Magenta ink M | Black ink K | Cyan ink C | Yellow ink Y |
| --- | --- | --- | --- | --- |
| Magenta dispersion liquid M | 4 | | | |
| Black dispersion liquid K | | 4 | | |
| Cyan dispersion liquid C | | | 4 | |
| Yellow dispersion liquid Y | | | | 4 |
| Sannix GP-250 | 12 | 12 | 12 | 12 |
| Tripropylene glycol monomethyl ether | 5 | 5 | 5 | 5 |
| Olfine E1010 | 1 | 1 | 1 | 1 |
| Aqueous dispersion of D-01 | 8 | 8 | 8 | 8 |
| Water | 70 | 70 | 70 | 70 |
| pH of ink | 8.5 | 8.6 | 8.5 | 8.5 |
| Surface tension of ink (mN/m) | 34.8 | 35.2 | 35.0 | 35.1 |

Sannix GP-250: organic solvent manufactured by Sanyo Chemical Industries, Ltd.
Olfine E1010: nonionic surfactant manufactured by Nissin Chemical Co., Ltd.

Test Example

<Evaluation of Cockling>

A GELJET GX5000 printer head manufactured by RICOH JAPAN Corp. was prepared. This printer head is a line head in which 96 nozzles are lined up. The printer head was fixed and disposed into an ink jet recording device having a structure described in FIG. 1 of JP2013-223960A.

At this time, the printer head was disposed such that the direction in which the 96 nozzles are lined up tilted by 75.7° with respect to the direction orthogonal to the movement direction of a stage of the ink jet recording device on the same plane.

In the following method, the ink droplets started to be ejected onto the aggregation-inducing layer of the image recording paper medium described above.

(Droplet Ejection Method)

In a state where the image recording paper medium was being moved at a constant speed in the movement direction of the stage, each of the black ink K, the cyan ink C, the magenta ink M and the yellow ink Y prepared as above was ejected from the printer head in a line method under the ejection conditions of an amount of ink droplet of 1.2 pL, an ejection frequency of 24 kHz, and resolution of 1200 dpi×1200 dpi (dot per inch) and a stage speed of 50 mm/s, so as to print a solid image in which dots of the respective colors were superposed on each other. More specifically, by forming a single-pass image of four colors on the central portion of the aggregation-inducing layer of the image recording paper medium under the aforementioned conditions, a 100% solid black image (2 cm×10 cm) was printed.

Immediately after printing, the image was dried for 3 seconds at 60° C. and then subjected to a fixing treatment at a nip pressure of 0.25 MPa and a nip width of 4 mm by being passed between a pair of fixing rollers heated to 60° C.

Thereafter, the cockling occurring immediately after fixing treatment was evaluated.

—Evaluation of Deformation of Recording Medium—

The image formed as above was visually observed, and the state of cockling occurred was evaluated according to the following evaluation criteria.

A: Cockling did not occur in the entirety of the image forming portion.

B: Although cockling occurred in a portion of the image forming portion, it was at an unproblematic level for practical use.

C: Cockling occurred over a wide range of the image forming portion.

D: Cockling occurred in the entire image forming portion.

The results are shown in the following Table 2.

<Evaluation of Dot Diameter>

A GELJET GX5000 printer head (manufactured by RICOH JAPAN Corp.) was prepared, and a storage tank connected thereto was refilled with the yellow ink Y prepared as above. The printer head was fixed and disposed into the ink jet recording device having the structure described in FIG. 1 of JP2013-223960A.

Specifically, the GELJET GX5000 printer head was fixed and disposed such that the direction (main scanning direction) of the line head, in which nozzles were lined up, tilted by 75.7° with respect to the direction orthogonal to the movement direction (sub-scanning direction) of the stage. Thereafter, in a state where the image recording paper medium provided with the aggregation-inducing layer as described above was being moved at a constant speed in the sub-scanning direction, the ink was ejected onto the aggregation-inducing layer in a line method under the ejection conditions of an amount of ink droplets of 2.4 pL, an ejection frequency of 24 kHz, and resolution of 1,200 dpi×1,200 dpi, thereby printing yellow dots.

Immediately after printing, the image was dried for 3 seconds at a temperature of 60° C. and subjected to a fixing treatment at a nip pressure of 0.25 MPa and a nip width of 4 mm by being passed between a pair of fixing rollers heated to 60° C., thereby obtaining an evaluation sample of a dot in which dot images are formed by the yellow ink.

In the obtained evaluation sample, twenty dots of yellow ink were randomly selected, the diameters thereof were measured by using a microscope, and the average thereof was determined as a dot diameter. From the dot diameter, a dot diameter of yellow dots, which were formed in the same manner as described above by using a paper medium obtained by forming an aggregation-inducing layer on a paper medium not containing the specific organic phosphorus compound (that is, a commercially available paper medium used as a raw material of the paper medium used as the test sample), was subtracted. In this way, a difference of a dot diameter was calculated and evaluated according to the following evaluation criteria. The difference of a dot diameter evaluated to be A or B is at a practical level.

—Evaluation of Dot Diameter—

A: The absolute value of the difference of a dot diameter was equal to or less than 3.0 μm.

B: The absolute value of the difference of a dot diameter was greater than 3.0 μm and equal to or less than 4.0 μm.

C: The absolute value of the difference of a dot diameter was greater than 4.0 μm and equal to or less than 5.0 μm.

D: The absolute value of the difference of a dot diameter was greater than 5.0 μm.

The results are shown in the following Table 2.

<Evaluation of Degree of Glossiness>

A GELJET GX5000 printer head (manufactured by RICOH JAPAN Corp.) was prepared, and a storage tank connected thereto was refilled with the black ink K prepared as above. The printer head was fixed and disposed into the ink jet recording device having the structure described in FIG. 1 of JP2013-223960A.

Specifically, the GELJET GX5000 printer head was fixed and disposed such that the direction (main scanning direction) of the line head, in which nozzles were lined up, tilted by 75.7° with respect to the direction orthogonal to the movement direction (sub-scanning direction) of the stage. Thereafter, in a state where the image recording paper medium provided with the aggregation-inducing layer as described above was being moved at a constant speed in the sub-scanning direction, the ink was ejected onto the aggregation-inducing layer in a line method under the ejection conditions of an amount of ink droplets of 2.4 pL, an ejection frequency of 24 kHz, and resolution of 1,200 dpi×1,200 dpi. In this way, a 100% solid black image was printed on the entire surface of the aggregation-inducing layer.

Immediately after printing, the image was dried for 3 seconds at a temperature of 60° C. and subjected to a fixing treatment at a nip pressure of 0.25 MPa and a nip width of 4 mm by being passed between a pair of fixing rollers heated to 60° C.

By using a gloss meter IG-410 (manufactured by HORIBA, LTD.), the obtained image was evaluated in terms of a degree of glossiness at an angle of 60° specified in JIS K5600. Specifically, based on a difference in a degree of glossiness (difference of a degree of glossiness) between the image obtained as above and a solid image obtained in the same manner as described above by using a recording medium, in which the aggregation-inducing layer was formed on a paper medium not containing the specific organic phosphorus compound (that is, a commercially available paper medium used as a raw material of the paper medium used as the test sample), the degree of glossiness was evaluated based on the following evaluation criteria. Herein, a degree of glossiness of an image using the image recording paper medium containing the specific organic phosphorus compound was equal to or higher than that of an image using the paper medium not containing the specific organic phosphorus compound.

—Evaluation of Degree of Glossiness—

A: The difference of a degree of glossiness was less than 1.

B: The difference of a degree of glossiness was equal to or greater than 1 and less than 3.

C: The difference of a degree of glossiness was equal to or greater than 3 and less than 5.

D: The difference of a degree of glossiness was equal to or greater than 5 and less than 10.

E: The difference of a degree of glossiness was equal to or greater than 10.

TABLE 2

| | Specific organic phosphorus compound | Paper medium (raw material) | Amount of specific organic phosphorus compound coating paper medium (g/m$^2$) | Amount of specific organic phosphorus compound contained in coat layer with respect to 100 parts of CaCO$_3$ (parts) | Evaluation Cockling | Dot diameter | Degree of glossiness |
|---|---|---|---|---|---|---|---|
| Example 1 | n-Propyl phosphonate | OK Topcoat + | 0.9 | 7 | B | A | A |
| Example 2 | t-butyl phosphonate | OK Topcoat + | 0.9 | 7 | B | A | A |
| Example 3 | Octyl phosphonate | OK Topcoat + | 0.9 | 7 | A | A | A |
| Example 4 | Decyl phosphonate | OK Topcoat + | 0.1 | 0.8 | B | A | A |
| Example 5 | Decyl phosphonate | OK Topcoat + | 0.5 | 4 | B | A | A |
| Example 6 | Decyl phosphonate | OK Topcoat + | 0.9 | 7 | A | A | A |
| Example 7 | Decyl phosphonate | OK Topcoat + | 1.8 | 14 | A | A | A |
| Example 8 | Decyl phosphonate | OK Topcoat + | 3.6 | 28 | A | A | B |
| Example 9 | Decyl phosphonate | OK Topcoat + | 5.2 | 40 | A | B | B |
| Example 10 | Decyl phosphonate | OK Topcoat + | 8.8 | 68 | A | B | B |
| Example 11 | Phenyl phosphonate | OK Topcoat + | 0.9 | 7 | B | A | A |
| Example 12 | Phenyl phosphonate | OK Topcoat + | 1.8 | 14 | A | A | A |
| Example 13 | 2-Ethylhexyl phosphate | OK Topcoat + | 0.9 | 6 | A | A | A |
| Example 14 | Dodecyl phosphate | OK Topcoat + | 0.9 | 7 | A | A | A |
| Example 15 | Dodecyl phosphate | OK Topcoat + | 1.8 | 14 | A | A | A |
| Example 16 | Oleyl phosphate | OK Topcoat + | 0.9 | 6 | B | A | A |
| Example 17 | Phenyl phosphate | OK Topcoat + | 1.8 | 14 | B | A | A |
| Example 18 | Dodecyl phosphate | OK Kinfuji + | 0.9 | 6 | A | A | A |
| Example 19 | Dodecyl phosphate | OK Coat L | 0.9 | 9 | A | A | A |
| Example 20 | Dodecyl phosphate | Aurora Coat | 0.9 | 8 | A | A | A |
| Example 21 | Dodecyl phosphate | Shiraoi | 2.7 | — | B | A | A |
| Example 22 | Dipotassium octyl phosphonate | OK Topcoat + | 1.8 | 14 | B | A | A |
| Example 23 | Disodium decyl phosphonate | OK Topcoat + | 1.8 | 14 | B | A | A |
| Example 24 | Dipotassium phenyl phosphonate | OK Topcoat + | 1.8 | 14 | B | A | A |
| Example 25 | Dodecyl phosphate dibutyl ethanolamine | OK Topcoat + | 1.8 | 14 | B | A | A |
| Example 26 | Monosodium phenyl phosphate | OK Topcoat + | 1.8 | 14 | A | A | A |
| Comparative example 1 | Hexamethylene diisocyanate | OK Topcoat + | 0.9 | 7 | D | A | A |
| Comparative example 2 | Hexamethylene diisocyanate | OK Topcoat + | 22.0 | 171 | B | A | E |
| Comparative example 3 | Megafac F-511 | OK Topcoat + | 0.9 | 7 | B | C | C |
| Comparative example 4 | Methylene diphosphonate | OK Topcoat + | 0.9 | 7 | D | C | A |
| Comparative example 5 | None | OK Topcoat + | — | — | D | A | A |

OK Kinfuji + (coated paper manufactured by Oji Paper Co., Ltd.)

OK Topcoat + (coated paper manufactured by Oji Paper Co., Ltd.)

OK Coat L (coated paper manufactured by Oji Paper Co., Ltd.)

Aurora Coat (coated paper manufactured by NIPPON PAPER INDUSTRIES CO., LTD.)

Shiraoi (non-coated paper manufactured by NIPPON PAPER INDUSTRIES CO., LTD)

Megafac F-511 (manufactured by DIC Corporation): perfluoroalkyl group-containing phosphoric acid ester-type amine neutralizer As shown in Table 2, in Comparative example 5 not containing the specific organic phosphorus compound, the entirety of the image forming portion was cockled (Comparative example 5). Furthermore, in Comparative example 1 containing hexamethylene diisocyanate instead of the specific organic phosphorus compound, the entirety of the image forming portion was cockled. It was understood that although the cockling can be inhibited to some extent by increasing the amount the hexamethylene diisocyanate coating the paper medium, the degree of glossiness then markedly increases in this case (Comparative example 2). In addition, even though the paper medium contained an organic phosphorus compound, in a case where the compound was not the organic phosphorus compound specified in the present invention, the dot diameter increased, the resolution deteriorated, and the inhibition of cockling and the inhibition of increase in the degree of glossiness could not be simultaneously accomplished (Comparative examples 3 and 4).

In contrast, it was understood that when the paper medium contains the specific organic phosphorus compound specified in the present invention, the cockling can be effectively inhibited, the dot diameter is small, the resolution is excellent, the degree of glossiness does not easily increase, and hence a high-quality image can be formed (Examples 1 to 26).

What is claimed is:

1. An image recording paper medium comprising a calcium carbonate-containing coat layer as a surface layer, wherein
the coat layer contains at least one of an organic phosphorus compound selected from an organic phosphonic acid represented by the following Formula (1), a salt of the organic phosphonic acid represented by the following Formula (1), an organic phosphoric acid represented by the following Formula (2), and a salt of the organic phosphoric acid represented by the following Formula (2),

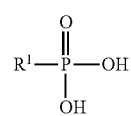

Formula (1)

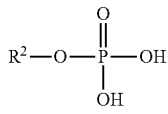

Formula (2)

$R^1$ represents an unsubstituted alkyl group, an unsubstituted cycloalkyl group, an unsubstituted alkenyl group, or an aryl group, and
$R^2$ represents an unsubstituted cycloalkyl group or an unsubstituted alkenyl group.

2. The image recording paper medium according to claim 1,
wherein the content of the organic phosphorus compound contained in the coat layer is 1 part by mass to 30 parts by mass with respect to 100 parts by mass of the content of the calcium carbonate contained in the coat layer.

3. The image recording paper medium according to claim 1 that is obtained by coating the coat layer of the paper medium with a solution containing the organic phosphorus compound.

4. An image recording method using the image recording paper medium according to claim 1, the method comprising:
a step (a) of coating a paper medium with a solution containing at least one of organic phosphorus compound selected from an organic phosphonic acid represented by the following Formula (1), a salt of the organic phosphonic acid represented by the following Formula (1), an organic phosphoric acid represented by the following Formula (2), and a salt of the organic phosphoric acid represented by the following Formula (2); and
a step (b) of forming an image by ejecting an aqueous ink by an ink jet method onto the surface of the paper medium that is coated with the solution,

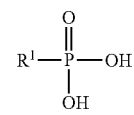

Formula (1)

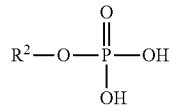

Formula (2)

wherein each of $R^1$ and $R^2$ independently represents an unsubstituted alkyl group, an unsubstituted cycloalkyl group, an unsubstituted alkenyl group, or an aryl group.

5. The image recording method according to claim 4, wherein each of $R^1$ and $R^2$ represents an unsubstituted alkyl group having 6 to 24 carbon atoms.

6. The image recording method according to claim 4, wherein in the step (a), the applied amount of the organic phosphorus compound is equal to or less than 10 g/m².

7. The image recording method according to claim 4, wherein the paper medium has a coat layer containing calcium carbonate, and
the step (a) is a step of coating the coat layer with a solution containing the organic phosphorus compound.

8. The image recording method according to claim 5, wherein the paper medium has a coat layer containing calcium carbonate, and
the step (a) is a step of coating the coat layer with a solution containing the organic phosphorus compound.

9. The image recording method according to claim 6, wherein the paper medium has a coat layer containing calcium carbonate, and
the step (a) is a step of coating the coat layer with a solution containing the organic phosphorus compound.

10. The image recording method according to claim 7, wherein the amount of the organic phosphorus compound coating the coat layer is 1 part by mass to 30 parts by mass with respect to 100 parts by mass of the content of the calcium carbonate contained in the coat layer.

11. The image recording method according to claim 8, wherein the amount of the organic phosphorus compound coating the coat layer is 1 part by mass to 30 parts by mass with respect to 100 parts by mass of the content of the calcium carbonate contained in the coat layer.

12. The image recording method according to claim 9, wherein the amount of the organic phosphorus compound coating the coat layer is 1 part by mass to 30 parts by mass with respect to 100 parts by mass of the content of the calcium carbonate contained in the coat layer.

13. The image recording method according to claim 4, further comprising:
   a step of fixing the formed image by heating after the step (b).

* * * * *